United States Patent [19]

Asato et al.

[11] 3,998,959
[45] Dec. 21, 1976

[54] SUBSTITUTED TETRAHYDRO-OXYBENZOTHIENYLUREA COMPOUNDS AS GROWTH PROMOTING AGENTS FOR ANIMALS

[75] Inventors: Goro Asato, Titusville; Terence James Bentley, S. Cranbury, both of N.J.

[73] Assignee: American Cyanamid Company, Stamford, Conn.

[22] Filed: Oct. 17, 1975

[21] Appl. No.: 623,233

[52] U.S. Cl. .......................... 424/275; 260/332.2 R
[51] Int. Cl.$^2$ ................ A61K 31/38; C07D 333/24
[58] Field of Search ............. 424/275; 260/132.9 F, 260/332.2 R

[56] References Cited

OTHER PUBLICATIONS

*Organic Chemistry,* Fieser & Fieser, 3rd Ed. (1960) pp. 136, 188 & 189, D. C. Heath and Company, Boston.

*Primary Examiner*—Frederick E. Waddell
*Attorney, Agent, or Firm*—Denis A. Polyn

[57] ABSTRACT

This invention relates to novel substituted 4,5,6,7-tetrahydro-7-oxybenzo[b]thien-4-ylurea compounds and a process for the preparation thereof. The compounds of this invention are useful as herbicidal agents and animal growth regulants.

14 Claims, No Drawings

SUBSTITUTED TETRAHYDRO-OXYBENZOTHIENYLUREA COMPOUNDS AS GROWTH PROMOTING AGENTS FOR ANIMALS

BACKGROUND OF THE INVENTION

The preparation of optically active intermediates is described in detail, in the Application for U.S. Letters Patent, Ser. No. 532,449; filed Dec. 13, 1974, and still pending of which Goro Asato is named as inventor, and which is incorporated herein by way of reference.

SUMMARY OF THE INVENTION

This invention relates to novel 4,5,6,7-tetrahydro-7-oxybenzo[b]thien-4-ylurea compounds represented by formula (I):

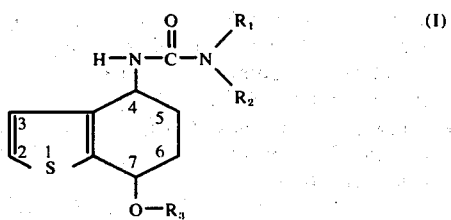

wherein $R_1$ is selected from the group consisting of hydrogen and alkyl $C_1$–$C_4$ (straight chain or branched); $R_2$ is selected from the group consisting of hydrogen, hydroxy, alkyl $C_1$–$C_4$ (straight chain or branched), alkenyl $C_3$–$C_4$, alkynyl $C_3$–$C_4$, and alkoxy $C_1$–$C_4$; $R_3$ is selected from the group consisting of alkyl $C_1$–$C_4$, alkenyl $C_3$–$C_4$, alkynyl $C_3$–$C_4$, alkanoyl $C_1$–$C_6$, $C_1$–$C_6$ halo-substituted alkanoyl, mono or disubstituted benzyl and mono or disubstituted benzoyl wherein said mono or disubstituted substituent is selected from the group consisting of methyl, methoxy, chloro, nitro and 2,4- and 3,4-dichloro; and wherein said compounds may be a racemic mixture of the cis and trans isomers and the optical isomers thereof.

A preferred embodiment of this invention consists of those compounds of formula (I), wherein $R_1$ and $R_2$ are selected from the group consisting of hydrogen and alkyl $C_1$–$C_4$; $R_3$ is selected from the group consisting of alkanoyl $C_1$–$C_6$ and methyl; and wherein said compounds are a racemic mixture of the cis and trans isomers and the optical isomers thereof.

In the compounds defined by formula (I), the terms cis and trans refer to the configuration of the —O—$R_3$ group with respect to the ureido group.

The term "halogen" is used to denote bromine, chlorine, fluorine and iodine.

This invention also relates to methods for the preparation of the compounds defined by formula (I), 4,5,6,7-tetrahydro-7-oxybenzo[b]thien-4-ylurea compounds, which may be a racemic mixture of the cis and trans isomers and/or the optically active isomers thereof.

The compounds of this invention can be conveniently prepared by a number of routes as hereafter described and illustrated in detail.

When a formula I urea is desired wherein $R_3$ is alkanoyl $C_1$–$C_6$, one mole equivalent of a hereinafter formula (II) 4,5,6,7-tetrahydro-7-hydroxybenzo[b]thien-4-ylurea compound is reacted with a 1 to 1½ mole equivalent of the appropriate $C_1$–$C_6$ alkanoic acid anhydride or halide (preferably the chloride) or with a mono or disubstituted benzoylchloride wherein said mono or disubstituted substituent is selected from the group consisting of methyl, methoxy, chloro, nitro, and 2,4- and 3,4-dichloro, in the presence of an inert organic solvent at a temperature in the range of 0° C to 100° C and preferably 10° C to 30° C for a period of time from 1 hour to several days or until the reaction is essentially complete.

Suitable organic solvents include aprotic solvents such as benzene, toluene, xylene; chlorinated hydrocarbon solvents such as methylene chloride, chloroform and dichloroethane; pyridine; ethers such as tetrahydrofuran, dimethoxyethane, diethylene glycol dimethyl ether and dioxane; ketones such as acetone, methyl ethyl ketone, methyl butyl ketone, methyl isobutyl ketone, or mixtures of said solvents.

When acid chlorides are employed in the above reaction, it is desirable to add an acid acceptor to the reaction mixture unless the solvent chosen is pyridine. Suitable acid acceptors include trialkylamines such as trimethyl- or triethylamine, pyridine and the like; alkali metal carbonates such as sodium or potassium carbonate; and strong basic ion exchange resins. The above reaction sequence can be illustrated as follows:

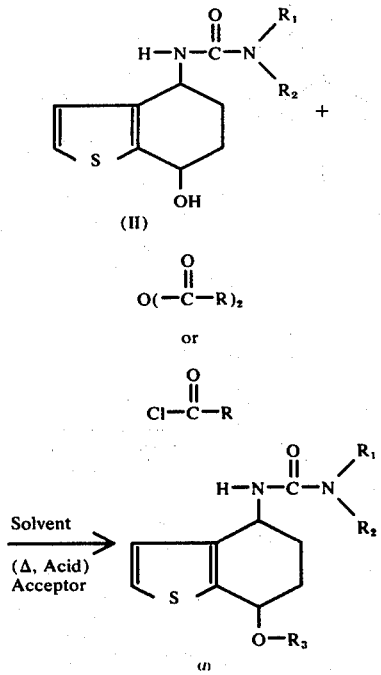

wherein $R_1$ and $R_2$ are as defined above with the proviso that $R_2$ cannot be OH; $R_3$ is alkanoyl $C_1$–$C_6$ or mono or disubstituted benzoyl wherein said mono or disubstituted substituent is selected from the group consisting of methyl, methoxy, chloro, nitro and 2,4- and 3,4-dichloro; and in the above equation the radical $$R-\overset{O}{\underset{\|}{C}}-$$

represents substituent $R_3$ as previously defined.

Formula (I), 4,5,6,7-tetrahydro-7-oxybenzo[b]thien-4-ylurea compounds, wherein $R_3$ represents alkyl $C_1-C_4$, alkenyl $C_3-C_4$ and alkynyl $C_3-C_4$ can be conveniently prepared by a number of routes, e.g.:

A formula (III) 4,5,6,7-tetrahydro-7-oxybenzo[b]thiophen-4-acetamide is reacted with a compound of the formula $R_3$-X in an inert solvent selected from the group hereinabove described in the presence of an acid acceptor such as silver oxide or sodium hydride for a period of time of from 1 hour to 2 days or until the reaction is essentially complete at a temperature range of from 10° C to 200° C and preferably 25° C to a maximum temperature determined by the boiling point of the $R_3$-X alkylating agent at atmospheric pressure, wherein X is chlorine, bromine and iodine and $R_3$ represents a member selected from the group consisting of alkyl $C_1-C_4$, alkenyl $C_3-C_4$, alkynyl $C_3-C_4$ and mono or disubstituted benzyl wherein said mono or disubstituted substituents are selected from the group consisting of methyl, methoxy, chloro, nitro and 2,4- and 3,4-dichloro. The thus obtained intermediate tetrahydro-7-alkoxybenzo[b]thiophen-4-acetamide of formula (IV) is hydrolyzed with an inorganic base selected from sodium or potassium hydroxide in an aqueous polar solvent to yield the corresponding thiophen-4-amine of formula (V). The above reaction sequence is graphically illustrated as follows:

Thus a formula (V) amine can be reacted with an equimolar to 1.5 mole excess of a carbamoyl halide of the formula

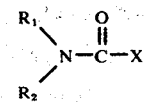

in an inert anhydrous organic solvent selected from the group consisting of benzene, toluene, xylene, methylene chloride, chloroform, dichloromethane, pyridine, tetrahydrofuran, diethylene glycol dimethyl ether, dioxane, acetone, methyl ethyl ketone and the like and mixtures thereof. In the above reaction, unless the solvent selected is pyridine, it is desirable to add acid acceptors such as $C_1-C_3$ trialkylamines, pyridine or alkali metal carbonates such as sodium or potassium carbonate or the like, for a period of time of from 1 hour to 24 hours, or until the reaction is essentially complete at a temperature range of from 0° C to 75° C and preferably 10° C to 30° C, and an inert gas, such as nitrogen, may be used if desired to blanket the reaction mixture. The above reaction can be graphically illustrated as follows:

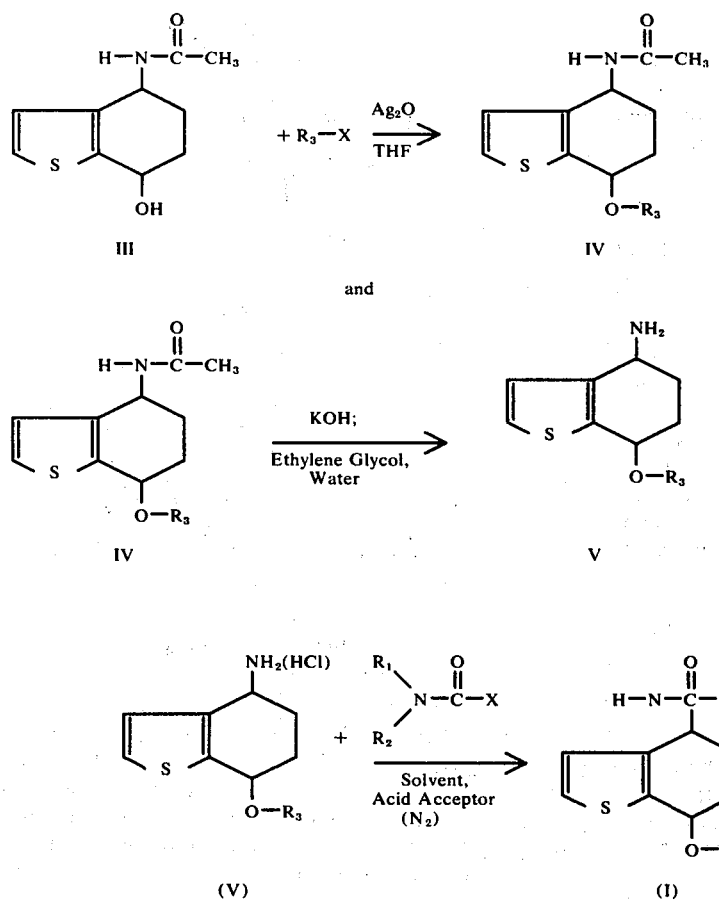

Formula (V) 4,5,6,7-tetrahydro-7-alkoxybenzo[b]thiophen-4-amine, wherein $R_3$ is as previously defined, is an intermediate common to a number of routes leading to the novel formula (I) 4,5,6,7-tetrahydro-7-oxybenzo[b]thien-4-ylurea compounds of the present invention.

wherein $R_1$ is alkyl $C_1-C_4$; $R_2$ is alkyl $C_1-C_4$; and $R_3$ is as previously defined.

A formula (V) amine (or its acid addition salt) can be reacted with a isocyanate of the formula $R_1$—NCO wherein $R_1$ is alkyl $C_1-C_4$, in approximately equimolar amounts affording formula I compounds wherein $R_1$ is alkyl $C_1-C_4$; $R_2$ is hydrogen; and $R_3$ is as defined above, however, it is generally preferably to employ from 5% to 50% excess of the isocyanate. The reaction can be conducted at a temperature in the range of 0° C to 100° C, but is preferably conducted 0° C to 70° C in the presence of an organic solvent.

Suitable organic solvents include aprotic aromatic solvents such as benzene, toluene and xylene; chlorinated hydrocarbon solvents such as methylene chloride, chloroform, and dichloroethane; ethers such as tetrahydrofuran, diethyl ether, dimethoxyethane, diethylene glycol dimethyl ether and dioxane, lower alkyl $C_1$–$C_4$ ketones, or mixtures of said solvents.

When in the above reaction the acid addition salt formula (V) amine is employed, it is desirable to add an acid acceptor to the reaction mixture. Suitable acid acceptors include trialkylamines such as trimethyl and triethylamine, pyridine or the like; alkali metal carbonates such as sodium and potassium carbonate; and strong basic ion exchange resins, and aqueous alkali in a 2 phase system using an immiscible hydrocarbon or chlorinated hydrocarbon solvent selected from the group of solvents above.

The above reaction may be graphically illustrated as follows:

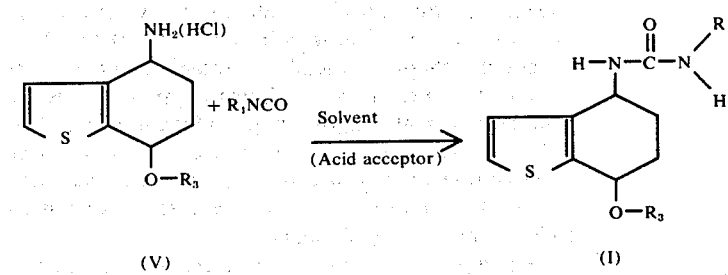

Formula (I) tetrahydro-7-oxybenzo[b]thien-4-ylurea compounds wherein $R_1$ and $R_2$ are hydrogen may be prepared from the above-identified formula (V) amine or its acid addition salt, by reacting said amine with an approximately equimolar amount of sodium or potassium isocyanate; however it is generally preferable to employ 5% to 50% excess of the isocyanate. The reaction can be conducted under the conditions described above in detail. Suitable solvents include water, polar solvents such as $C_1$–$C_3$ alcohols, tetrahydrofuran, dioxane, acetone, methylethyl ketone and the like and mixtures thereof; in the pH range of 5 to 7 and preferably at pH 6. The above reaction may be graphically illustrated as follows:

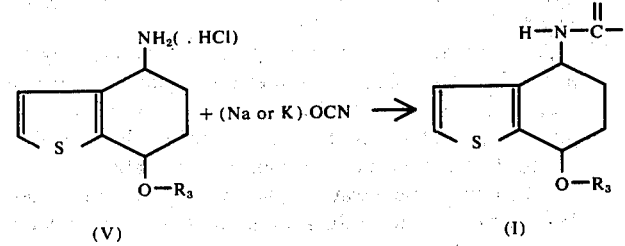

Formula (I) tetrahydro-7-oxybenzo[b]thien-4-ylurea compounds can also be prepared by reacting approximately equimolar amounts of a formula (VI) tetrahydro-7-oxybenzo[b]thienyl isocyanate and an appropriately substituted

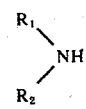

amine or an acid addition salt thereof.

In practice the formula (VI) isocyanate is readily prepared from a formula (V) amine or its acid addition salt by reacting the same with phosgene under anhydrous conditions, e.g., a blanket of inert gas such as nitrogen. The reaction is initially carried out at a temperature between about 0° C to 40° C, preferably 10° C to 20° C, and then heated to between about 50° C and 100° C, preferably 60° C to 80° C. The reaction is usually carried out in the presence of an organic solvent such as benzene, toluene or xylene. The formula (VI) tetrahydro-7-oxybenzo[b]thienyl isocyanate is next reacted with the formula

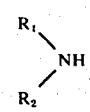

amine in the presence of a solvent, such as described above, at a temperature between 0° C and 80° C. When a

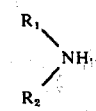

amine salt is used, it is of advantage to introduce into the reaction mixture an acid acceptor such as described above.

The above reaction sequence may be graphically illustrated as follows:

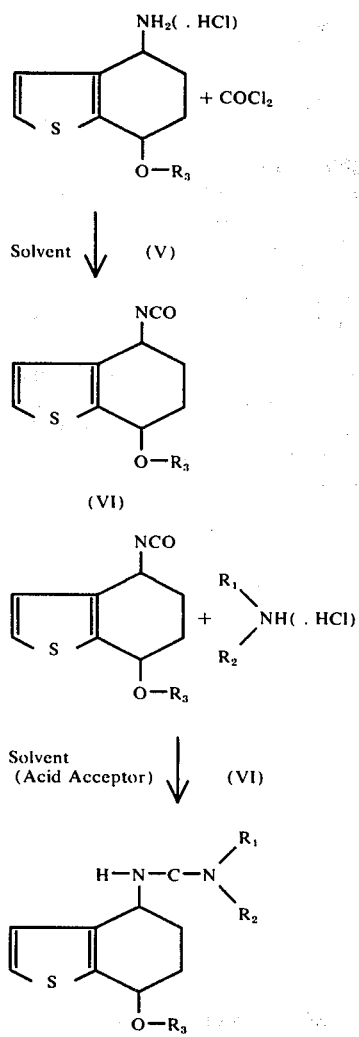

wherein $R_1$, $R_2$ and $R_3$ are as previously defined.

The formula (I) 4,5,6,7-tetrahydro-7-oxybenzo[b]-thien-4-ylurea compounds (cis and trans) obtained by the above procedure are racemic (dl) mixtures. Should the optically active isomers of formula (I) compounds be desired, these may be conveniently obtained from the resolved (optically active) intermediates by the above procedures.

The compounds of the present invention represented and defined by formula I above are useful as growth-promoting agents for animals such as poultry, fur-bearing and farm animals, and the use of said compounds for this purpose provides the added advantage of improving feed conversion for said animals. The term "feed conversion" means the ratio of unit weight of feed per unit weight of gain, and improvement in feed conversion means increased weight gain from a given unit of feed consumed.

In practice, an effective amount of a formula (I) 4,5,6,7-tetrahydro-7-oxybenzo[b]thien-4-ylurea compound or a physiologically active optical isomer thereof is administered orally or parenterally to the host animal.

For oral administration a formula (I) compound or its optically active isomer is blended in, or is given with the feed of the above-said host animal in an amount equivalent to between 0.0001% to 0.08% and preferably 0.001% to 0.04% by weight of feed.

The active material can be conveniently formulated as a premix and/or animal feed supplement which is then admixed with a nutritionally balanced feed or added thereto as a top dressing, or the like.

Premixes may be prepared by blending about 70% to 99% by weight of ground corn, ground rice hulls, rice flour, or the like with about 1% to 30% by weight of a formula (I) tetrahydro-7-oxybenzo[b]thien-4-ylurea compound or an optically active isomer thereof.

The growth rate of animals is also improved when a formula (I) tetrahydro-7-oxybenzo[b]thien-4-ylurea compound or an optically active isomer thereof is administered as a subcutaneous implant under the skin of the animal. Implants are generally in the form of a paste or pellet which permits the active compound to be released into the bloodstream of the animal over an extended period of time; as for example, from several weeks to several months.

Whether the implant is in the form of a paste or a pellet is a matter of choice. Pellet-type implants which can be used in accordance with this invention may be prepared by admixing from about 50% to 95% by weight of a formula (I) tetrahydro-7-oxybenzo[b]thien-4-ylurea compound with from about 50% to 5% by weight of a pharmaceutically acceptable carrier such as Castor wax (i.e., glyceryl 12-hydroxystearate), white wax, bees wax, starch, or a high molecular weight (i.e. 4,000) polyethylene glycol, or mixtures thereof, alone or in combination with small amounts of formulation aids such as zinc or magnesium stearate, polyvinylpyrrolidone and dibutylphthalate.

Paste implants can be prepared using the same percentages of drug as stated above, but employing a mixture of high (i.e., 4,000) and low (i.e., 400) molecular weight polyethylene glycol alone, or in combination with, Castor wax, bees wax and/or polyvinylpyrrolidone.

Implants may vary in size and weight, but usually range between 10 mg and 100 mg per implant. Advantageously, with this method of application, the drug can be administered at periodic intervals throughout the feeding period of the animals. Formulations and intervals between implantations can be varied to provide a daily drug release of generally about 0.0005 mg to 0.2 mg per kg of body weight, and preferably 0.001 mg to 0.1 mg per kg of body weight.

The compounds of this invention are also useful as herbicidal agents effective for the control of a wide variety of undesirable broadleaf weeds and grass weeds.

As herbicidal agents, the active compounds may be applied to the foliage of undesirable plants or to soil containing seeds of undesirable plants. They may be applied in solid or liquid form, but preferably applied in a liquid spray; as for example, as a wettable powder, emulsifiable concentrate or the like which is dispersed in water or another diluent, and applied to the foliage or soil in dilute solution. In practice, generally from 0.15 kg to 11.2 kg per hectare of the active compound will provide control of undesirable plants.

The invention in the present application is further illustrated by the non-limiting examples set forth below.

EXAMPLE 1

Preparation of 4,5,6,7-Tetrahydro-7-acetoxybenzo[b]thien-4-ylurea

Two g (9.43 mm) of 4,5,6,7-tetrahydro-7-hydroxybenzo[b]thien-4-ylurea is stirred for 2 days at room temperature with acetic anhydride (5 ml) and pyridine (10 ml). The excess reagents are removed in vacuo, the resulting gum dissolved in methylene chloride (50 ml), the solution washed with water (50 ml), the water wash counter extracted with methylene chloride (25 ml), the combined methylene chloride layers dried with sodium sulfate and evaporated. The resulting gum is treated with ethyl acetate ($\approx$5 ml) to afford a first crop (1.15 g, 48% Y) of the title compound, m.p. 168° C–170° C, dec. and a second crop (0.58 g, 24% Y) m.p. 166° C–172° C, dec. The analytical sample crystallized from ethyl acetate has m.p. 165° C–168° C dec. The isomeric compound prepared in the same manner melts at 182° C–184° C.

Similarly, the levorotatory 4,5,6,7-tetrahydro-7-hydroxybenzo[b]thien-4-ylurea is treated with acetic anhydride to give the optically active 4,5,6,7-tetrahydro-7-acetoxybenzo[b]thien-4-ylurea.

EXAMPLE 2

Preparation of 4,5,6,7-Tetrahydro-7-benzoyloxybenzo[b]thien-4-ylurea

In 5 ml of pyridine, 0.53 g of 4,5,6,7-tetrahydro-7-hydroxybenzo[b]thien-4-ylurea is stirred and 0.39 g of benzoyl chloride added under a nitrogen atmosphere. The mixture is stirred at room temperature and after 1 hr, an additional 0.2 g of benzoyl chloride is added. After another 0.75 hr, the mixture is poured into $H_2O$ and the white precipitate is collected. The solid is washed with $H_2O$, dried, dissolved in acetone-hexane and filtered to remove an insoluble material. The filtrate is evaporated to dryness and the acetone-hexane treatments are repeated twice to remove additional side product. The solid from the filtrate is recrystallized from ethyl acetate to give a solid with m.p. 199° C–205° C.

The remaining mother liquid is evaporated to dryness and the residue crystallized from ethyl acetate to afford the title compound, which is washed with ethyl acetate and then ethyl acetate - hexane to afford crystals, m.p. 169° C–171° C dec.

EXAMPLE 3 – 15

By the method of Example 1 and using the appropriate acid anhydrides and 7-hydroxybenzothien-4-ylureas, the following compounds are prepared:

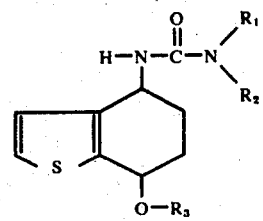

| Example | $R_1$ | $R_2$ | $R_3$ |
|---------|-------|-------|-------|
| 3 | H | $CH_3$ | $CH_3$—CO |
| 4 | $CH_3$ | $CH_3$ | $CH_3$—CO |
| 5 | H | $C_2H_5$ | $CH_3$—CO |
| 6 | H | H | $C_3H_7$—CO |
| 7 | H | $CH_3$ | $C_2H_5$—CO |
| 8 | H | H | $HCCl_2$—CO |
| 9 | H | H | $CF_3$—CO |
| 10 | H | $CH_3$ | $Cl$—$CH_2$—CO |
| 11 | H | i-$C_3H_7$ | $CH_3$—CO |
| 12 | H | $C_2H_5$ | $C_5H_{11}$—CO |
| 13 | $C_4H_9$ | $C_4H_9$ | $CH_3$—CO |
| 14 | H | $CH_2$—C≡CH | $CH_3$—CO |
| 15 | H | $CH_2$—CH=$CH_2$ | $CH_3$—CO |

EXAMPLE 16 – 31

By the method of Example 2 and using the appropriate substituted benzoyl chloride and 7-hydroxybenzothien-4-ylureas, the following benzoyloxy compounds are prepared:

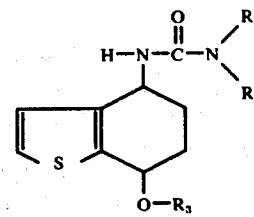

| Example | $R_1$ | $R_2$ | $R_3$ |
|---------|-------|-------|-------|
| 16 | H | H | 4-Cl-$C_6H_4$—CO |
| 17 | H | $CH_3$ | 3-Cl-$C_6H_4$—CO |
| 18 | H | $C_4H_9$ | 2-Cl-$C_6H_4$—CO |
| 19 | H | H | 4-$O_2N$-$C_6H_4$—CO |
| 20 | $CH_3$ | $CH_3$ | 3-$NO_2$-$C_6H_4$—CO |

-continued

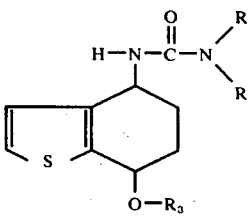

| Example | R₁ | R₂ | R₃ |
|---|---|---|---|
| 21 | CH₃ | H |  |
| 22 | H | H |  |
| 23 | H | H | 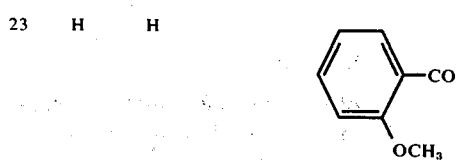 |
| 24 | H | H |  |
| 25 | H | CH₃ | 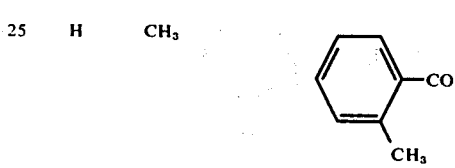 |
| 26 | H | H |  |
| 27 | H | H |  |
| 28 | H | H | 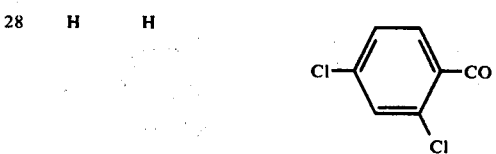 |
| 29 | C₄H₉ | C₄H₉ | 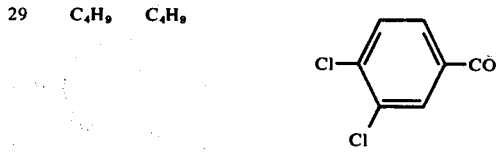 |
| 30 | H | CH₂—C≡CH | 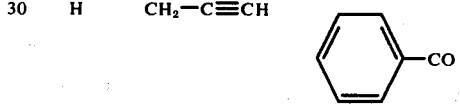 |

-continued

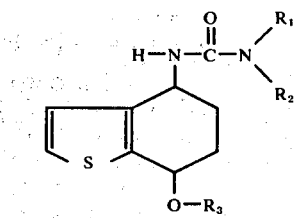

| Example | R₁ | R₂ | R₃ |
|---|---|---|---|
| 31 | H | CH₂—CH=CH₂ | 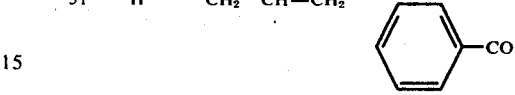 |

EXAMPLE 32

Preparation of 4,5,6,7-Tetrahydro-7-methoxybenzo[b]thien-4-ylacetamide

Eight g (37.86 mm) of 4,5,6,7-tetrahydro-7-hydroxybenzo[b]thien-4-ylacetamide and methyl iodide (28 ml, 0.45 M) are stirred in tetrahydrofuran (160 ml). The suspension is treated with silver oxide (60 g, 0.259 M) added in portions over a period of 5 hours. The reaction mixture is stirred overnight, filtered through celite, the cake is washed with tetrahydrofuran (2 × 100 ml) and dichloromethane (100 ml) and the filtrate evaporated to afford the crude title compound as a yellow-orange solid (8.1 g, 95% Y) m.p. 108° C–113° C dec. Two recrystallizations from acetone/hexane afford the analytical specimen, m.p. 124° C–126° C dec.

Similarly, substitution of the two levorotatory diastereomers of 4,5,6,7-tetrahydro-7-hydroxybenzo[b]thien-4-yl-acetamide for the dl acetamide affords the respective optically active title compounds.

EXAMPLE 33

Preparation of 4,5,6,7-Tetrahydro-7-methoxybenzo[b]thien-4-ylurea

Four g (17.78 mm) of 4,5,6,7-tetrahydro-7-methoxybenzo[b]thien-4-ylacetamide, ethylene glycol (42 ml) and a solution of potassium hydroxide (18 g, 0.28 M) in water (18 ml) are stirred and refluxed under nitrogen overnight. The cooled solution is treated with water (200 ml) and extracted thrice with methylene chloride (total volume 250 ml). The organic extracts are combined, washed with 10% sodium hydroxide (50 ml), dried with sodium sulfate and evaporated to afford the amine as a brown oil (3.4 g).

The amine is suspended in water (20 ml) and dilute hydrochloric acid added dropwise to the cooled suspension until the pH is ~6. After filtration through glass wool the filtrate is treated with a solution of potassium cyanate (3.5 g ~43 mm) in water (10 ml) and the mixture stirred overnight. Filtration of the precipitated white solid followed by thorough washing with water and air drying affords the title compound (3.32 g, 83% Y) m.p. 198° C–200.5° dec. The analytical specimen recrystallized from acetone has m.p. 203° C–204° C dec.

Similarly, optically active 4,5,6,7-tetrahydro-7-methoxybenzo[b]thien-4-ylacetamide affords optically active 4,5,6,7-tetrahydro-7-methoxybenzo[b]thien-4-ylurea.

EXAMPLE 34

Preparation of 3-(4,5,6,7-Tetrahydro-7-methoxybenzo[b]thien-4-yl)-1-methylurea

Crude 4,5,6,7-tetrahydro-7-methoxybenzo[b]thiophen-4-amine (2.3 g, 12.57 mm) is dissolved in ether (50 ml) and the stirred solution treated with a solution of methyl isocyanate (2.9 ml) in ether (10 ml), added over a period of 20 minutes. After stirring overnight the product is filtered off, washed twice with ether (50 ml total) and air dried to afford the title compound (2.25 g, 75% Y) m.p. 152° C–159° C. The analytical sample is recrystallized from acetone and has m.p. 164° C–166° C.

EXAMPLE 35

By the method of Example 32, 4,5,6,7-tetrahydro-7-hydroxybenzo[b]thien-4-ylacetamide is alkylated with the following R-X (where X=Cl, Br, or I) to afford 4,5,6,7-tetrahydro-7-alkoxybenzo[ ]thien-4-ylacetamides.

| RX | $R_3$ |
|---|---|
| $C_2H_5I$ | $C_2H_5$ |
| n-$C_3H_7I$ | $C_3H_7$ |
| n-$C_4H_9I$ | $C_4H_9$ |
| $C_6H_5CH_2I$ | $C_6H_5CH_2$ |
| $C_6H_5CH_2Cl$ | $C_6H_5CH_2$ |
| $H_2C=CH-CH_2Br$ | $H_2C=CH-CH_2$ |
| $HC\equiv C-CH_2Br$ | $H-C\equiv C-CH_2$ |

EXAMPLE 36

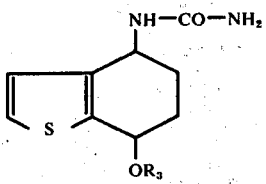

By the method of Example 33, the products derived in Example 35 are converted to compounds of the above structure where $R_3 = C_2H_5$, n-$C_3H_7$, n-$C_4H_9$, $C_6H_5CH_2$, $H_2C=CH-CH_2$, and $HC\equiv C-CH_2$.

EXAMPLE 37

By the method of Example 34, 4,5,6,7-tetrahydro-7-methoxybenzo[b]thiophen-4-amine is allowed to react with the following isocyanates to afford substituted ureas.

| Isocyanate | $R_2$ (Urea) |
|---|---|
| $C_2H_5NCO$ | $C_2H_5$ |
| iso-$C_3H_7NCO$ | iso-$C_3H_7$ |
| n-$C_4H_9NCO$ | n-$C_4H_9$ |
| $H_2C=CH-CH_2-NCO$ | $H_2C=CH-CH_2$ |

EXAMPLE 38

Preparation of 4,5,6,7-Tetrahydro-7-methoxybenzo[b]thien-4-ylisocyanate

A 1 g sample of 4,5,6,7-tetrahydro-7-methoxybenzo[b]thiophen-4-amine is added to 18 ml of 12.5% phosgene solution (benzene) in a nitrogen atmosphere at 20° C. After stirring at room temperature for an hour, the mixture is heated to 60° C and kept at this temperature for 7 hours. The mixture is cooled to room temperature and evaporated to dryness in vacuo to afford the crude 4,5,6,7-tetrahydro-7-methoxybenzo[b]thien-4-ylisocyanate.

EXAMPLE 39

Preparation of 1,1-Dimethyl-3-(4,5,6,7-tetrahydro-7-methoxybenzo[b]thien-4-yl)urea A 1 g sample of 4,5,6,7-tetrahydro-7-methoxybenzo[b]thien-4-ylisocyanate in 10 ml of dry dichloromethane under nitrogen atmosphere is treated with 2 ml of 40% aqueous dimethylamine at ice-bath temperature. The mixture is stirred for 2 hours at room temperature, the mixture evaporated to dryness, and the title product is collected and washed with water.

The identical product is obtained when 4,5,6,7-tetrahydro-7-methoxybenzo[b]thiophen-4-amine is allowed to react with dimethylcarbamoyl chloride in dichloromethane in the presence of triethylamine.

Similarly, 4,5,6,7-tetrahydro-7-methoxybenzo[b]thien-4-ylisocyanate is allowed to react with propargylamine, methoxyamine, hydroxylamine, n-butoxyamine and methylmethoxyamine to afford 1-propynyl-, 1-methoxy-, 1-hydroxy-, 1(-n-butoxy)-, and 1-methyl-1-methoxy-3-(4,5,6,7-tetrahydrobenzo[b]thien-4-yl)urea, respectively.

EXAMPLE 40

Preparation of 4,5,6,7-Tetrahydro-7-benzyloxybenzo[b]thien-4-ylacetamide

A sample (0.5 g) of 4,5,6,7-tetrahydro-7-hydroxybenzo[b]thien-4-ylacetamide is suspended in 20 ml of dry tetrahydrofuran under a nitrogen atmosphere and the mixture is cooled in an ice bath while 2.1 equivalents or 120 mg of 57% sodium hydride in an oil dispersion is added. The mixture is then stirred at room temperature for an hour and 5 ml of dry N,N-dimethylformamide is added to facilitate dissolution of the sodium hydride. After stirring for an hour, the mixture is cooled in an ice bath and 330 mg of benzyl chloride in 5 ml of dry tetrahydrofuran is added dropwise. The bath is removed and the mixture is stirred at room temperature for several hours. It is then warmed (below boiling point) for an overnight period. Water (25 ml) is carefully added to the reaction mixture and the solvents are stripped off on a rotary evaporator. The residue (yellowish semisolid) is dissolved in dichloromethane and water is added. The dichloromethane layer is collected and the aqueous portion is further extracted with dichloromethane. The combined dichloromethane solutions are washed with 2N hydrochloric acid, water, and dried (magnesium sulfate). The solution is then evaporated in vacuo and the residue is triturated with diethyl oxide. The title product is collected and washed with diethyl oxide to afford 320 mg, m.p. 139° C to 143° C.

Similarly, the following 7-substituted benzyloxy compounds are obtained by using the corresponding substituted benzyl bromide or chloride:

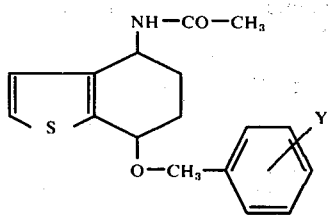

where Y = 2-Cl, 3-Cl, 4Cl, 2-$CH_3$, 3-$CH_3$, 4-$CH_3$, 2-$CH_3O$, 3-$CH_3O$, 4-$CH_3O$, 2-nitro, 3-nitro, 4-nitro, 2,4-dichloro, and 3,4-dichloro.

EXAMPLE 41

By the method described in Example 33, the following 4,5,6,7-tetrahydro-7-substituted benzyloxybenzo[b]thien-4-yl-urea are prepared from the corresponding acetamides described in Example 40.

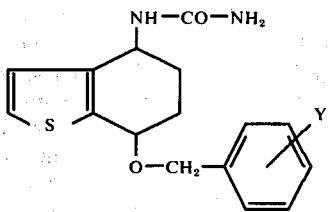

where Y = 2-Cl, 3-Cl, 4-Cl, 2-$CH_3$, 3-$CH_3$, 4-$CH_3$, 2-$CH_3O$, 3-$CH_3O$, 4-$CH_3O$, 2-nitro, 3-nitro, 4-nitro, 2,4-dichloro, and 3,4-dichloro.

EXAMPLE 42

Mouse Growth Regulant Tests

CFI female mice from Carworth Farm are received when they are 6 weeks old. They are housed 10 to a cage in air-conditioned rooms (72° F to 76° F) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of 10 and assigned at random to the different treatments. The concentration of the different compounds in the diet is indicated in the following Tables. Twelve days later the mice are weighed again and the experiment terminated. At least 3 cages (30 mice) of untreated controls are included in each test. Test data are provided in Table I below wherein data are reported as percent weight gain over controls. The following is a description of the diet to which the growth promoting compounds are added.

| DIET | |
|---|---|
| Guaranteed Analysis | |
| Crude protein not less than | 23.0% |
| Crude fat not less than | 4.5% |
| Crude fiber not more than | 6.0% |
| Ash not more than | 9.0% |
| Ingredients | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

Table I

Effectiveness of 4,5,6,7-Tetrahydro-7-oxybenzo[b]thien-4-yl-ureas as Animal Growth Promoting Agents, Reported as Percent Weight Gain Over Controls Using Mice as the Test Animal

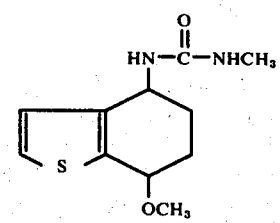

| Rate ppm in Diet | $R_3$ | % Weight Gain Over Controls |
|---|---|---|
| 400 | $CH_3$—CO | 64.6 |
| 400 | $CH_3$—CO (geometrical isomer) | 69.7 |
| 400 | n-$C_5H_{11}$CO | 89.2 |
| 200 | $CH_3$ | 70.8 |

[Structure: HN—C(=O)—NHCH$_3$ substituted benzo[b]thienyl with OCH$_3$]

| Rate ppm in Diet | $R_3$ | % Weight Gain over Controls |
|---|---|---|
| 400 | — | 80 |

We claim:
1. A compound of the formula:

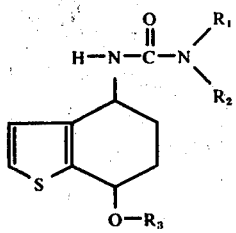

wherein $R_1$ is selected from the group consisting of hydrogen and $C_1$–$C_4$ alkyl; $R_2$ is selected from the group consisting of hydrogen, hydroxy, $C_1$–$C_4$ alkyl, $C_3$–$C_4$ alkenyl, $C_3$–$C_4$ alkynyl and $C_1$–$C_4$ alkoxy; $R_3$ is selected from the group consisting of $C_1$–$C_4$ alkyl, $C_3$–$C_4$ alkenyl, $C_3$–$C_4$ alkynyl, $C_1$–$C_6$ alkanoyl, $C_1$–$C_6$ halo-substituted alkanoyl, mono or disubstituted benzyl and mono or disubstituted benzoyl wherein said mono or disubstituted substituent is selected from the group consisting of methyl, methoxy, chloro, nitro and 2,4- and 3,4-dichloro; and the racemic mixture of the cis and trans isomers and the optical isomers thereof.

2. A compound according to claim 1, wherein $R_1$ and $R_2$ are selected from the group consisting of hydrogen and $C_1$–$C_4$ alkyl; $R_3$ is selected from the group consisting of alkanoyl $C_1$–$C_6$ and methyl; and the racemic mixture of the cis and trans isomers and the optical isomers thereof.

3. The racemic mixture according to claim 1, cis- and trans-4,5,6,7-tetrahydro-7-acetoxybenzo[b]thien-4-ylurea.

4. The optical isomers according to claim 1, cis- and trans-4,5,6,7-tetrahydro-7-acetoxybenzo[b]thien-4-ylurea.

5. The racemic mixture according to claim 1, cis- and trans-4,5,6,7-tetrahydro-7-methoxybenzo[b]thien-4-ylurea.

6. The optical isomers according to claim 1, cis- and trans-4,5,6,7-tetrahydro-7-methoxybenzo[b]thien-4-ylurea.

7. The racemic mixture according to claim 1, cis- and trans-1-methyl-3-(4,5,6,7-tetrahydro-7-acetoxybenzo[b]thien-4yl)urea.

8. The optical isomers according to claim 1, cis- and trans-1-methyl-3-(4,5,6,7-tetrahydro-7-acetoxybenzo[b]thien-4-yl)urea.

9. A method for improving feed efficiency and enhancing the growth rate of a veterinary homothermic animal which comprises administering to said animal an effective amount of a compound of the formula:

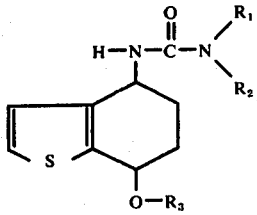

wherein $R_1$ is selected from the group consisting of hydrogen and $C_1$–$C_4$ alkyl; $R_2$ is selected from the group consisting of hydrogen, hydroxy, $C_1$–$C_4$ alkyl, $C_3$–$C_4$ alkenyl, $C_3$–$C_4$ alkynyl and $C_1$–$C_4$ alkoxy; $R_3$ is selected from the group consisting of $C_1$–$C_4$ alkyl, $C_3$–$C_4$ alkenyl, $C_3$–$C_4$ alkynyl, $C_1$–$C_6$ alkanoyl, $C_1$–$C_6$ halo-substituted alkanoyl, mono or disubstituted benzyl and mono or disubstituted benzoyl wherein said mono or disubstituted substituent is selected from the group consisting of methyl, methoxy, chloro, nitro and 2,4- and 3,4-dichloro; and the racemic mixture of the cis and trans isomers and the optical isomers thereof.

10. A method for enhancing the growth of poultry, farm and fur-bearing animals, which comprises administering to said animals, orally or parenterally, a growth-promoting amount of a compound of the formula:

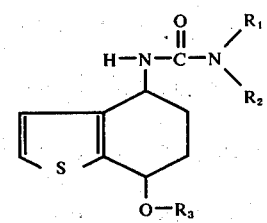

wherein $R_1$ is selected from the group consisting of hydrogen and $C_1$–$C_4$ alkyl; $R_2$ is selected from the group consisting of hydrogen, hydroxy, $C_1$–$C_4$ alkyl, $C_3$–$C_4$ alkenyl, $C_3$–$C_4$ alkynyl and $C_1$–$C_4$ alkoxy; $R_3$ is selected from the group consisting of $C_1$–$C_4$ alkyl, $C_3$–$C_4$ alkenyl, $C_3$–$C_4$ alkynyl, $C_1$–$C_6$ alkanoyl, $C_1$–$C_6$ halo-substituted alkanoyl, mono or disubstituted benzyl and mono or disubstituted benzoyl wherein said mono or disubstituted substituent is selected from the group consisting of methyl, methoxy, chloro, nitro and 2,4- and 3,4-dichloro; and the racemic mixture of the cis and trans isomers and the optical isomers thereof.

11. A method according to claim 10, wherein said compound is orally administered to said animals in an amount equivalent to between 0.0001% and 0.08% by weight of animal feed.

12. A method according to claim 10, wherein said compound is parenterally administered as one or more subcutaneous implants beneath the skin of said animal whereby said implants provide a daily drug release of from about 0.0005 mg to about 0.2 mg of said compound per kg of animal body weight.

13. An animal feed composition for improving feed efficiency and enhancing the growth rate of poultry, farm and fur-bearing animals, which comprises a nutritionally balanced diet containing from about 0.0001% to about 0.08% by weight of a compound of the formula:

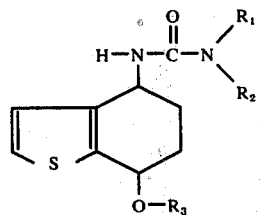

wherein $R_1$ is selected from the group consisting of hydrogen and $C_1$–$C_4$ alkyl; $R_2$ is selected from the group consisting of hydrogen, hydroxy, $C_1$–$C_4$ alkyl, $C_3$–$C_4$ alkenyl, $C_3$–$C_4$ alkynyl and $C_1$–$C_4$ alkoxy; $R_3$ is selected from the group consisting of $C_1$–$C_4$ alkyl, $C_3$–$C_4$ alkenyl, $C_3$–$C_4$ alkynyl, $C_1$–$C_6$ alkanoyl, $C_1$–$C_6$ halo-substituted alkanoyl, mono or disubstituted benzyl and mono or disubstituted benzoyl wherein said mono or disubstituted substituent is selected from the group consisting of methyl, methoxy, chloro, nitro and 2,4- and 3,4-dichloro; and the racemic mixture of the cis and trans isomers and the optical isomers thereof.

14. An animal feed premix for enhancing the growth rate of poultry, farm and fur-bearing animals, which comprises from about 70% to about 99% by weight of an edible carrier and from about 1% to about 30% by weight of a compound of the formula:

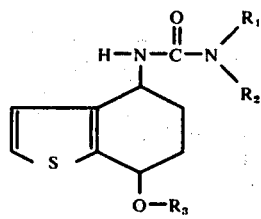

wherein $R_1$ is selected from the group consisting of hydrogen and $C_1$–$C_4$ alkyl; $R_2$ is selected from the group consisting of hydrogen, hydroxy, $C_1$–$C_4$ alkyl, $C_3$–$C_4$ alkenyl, $C_3$–$C_4$ alkynyl and $C_1$–$C_4$ alkoxy; $R_3$ is selected from the group consisting of $C_1$–$C_4$ alkyl, $C_3$–$C_4$ alkenyl, $C_3$–$C_4$ alkynyl, $C_1$–$C_6$ alkanoyl, $C_1$–$C_6$ halo-substituted alkanoyl, mono or disubstituted benzyl and mono or disubstituted benzoyl wherein said mono or disubstituted substituent is selected from the group consisting of methyl, methoxy, chloro, nitro and 2,4- and 3,4-dichloro; and the racemic mixture of the cis and trans isomers and the optical isomers thereof.

* * * * *